United States Patent [19]
Rogers

[11] 3,944,180
[45] Mar. 16, 1976

[54] SUPPORTING APPARATUS FOR INTRAVENOUS CONTAINERS OR THE LIKE

[75] Inventor: Gerald L. Rogers, Webster Groves, Mo.

[73] Assignee: Chemetron Corporation, Chicago, Ill.

[22] Filed: Apr. 26, 1974

[21] Appl. No.: 464,361

[52] U.S. Cl. .................................. 248/323; 16/96 R
[51] Int. Cl.² ............................................ A47K 1/08
[58] Field of Search ........... 248/295, 298, 307, 323, 248/324, 325, 327, 333, 335, 336, 337; 211/113; 16/96 D, 96 R

[56] References Cited
UNITED STATES PATENTS

| 150,861 | 5/1874 | Hull | 248/336 |
|---|---|---|---|
| 405,899 | 6/1889 | Maschmeyer | 248/336 |
| 1,889,112 | 11/1932 | Shoemaker | 16/96 R X |
| 3,734,441 | 5/1973 | Lux | 248/295 X |

FOREIGN PATENTS OR APPLICATIONS

| 921,002 | 3/1963 | United Kingdom | 248/323 |
|---|---|---|---|
| 382,757 | 10/1923 | Germany | 248/307 |

Primary Examiner—William H. Schultz
Attorney, Agent, or Firm—N. M. Esser

[57] ABSTRACT

An apparatus including a track which may have square corners, a carriage therefor, a carriage braking device, and a container holder supported from the carriage, wherein the holder may be quickly located in a desired position and maintained in this position.

5 Claims, 8 Drawing Figures

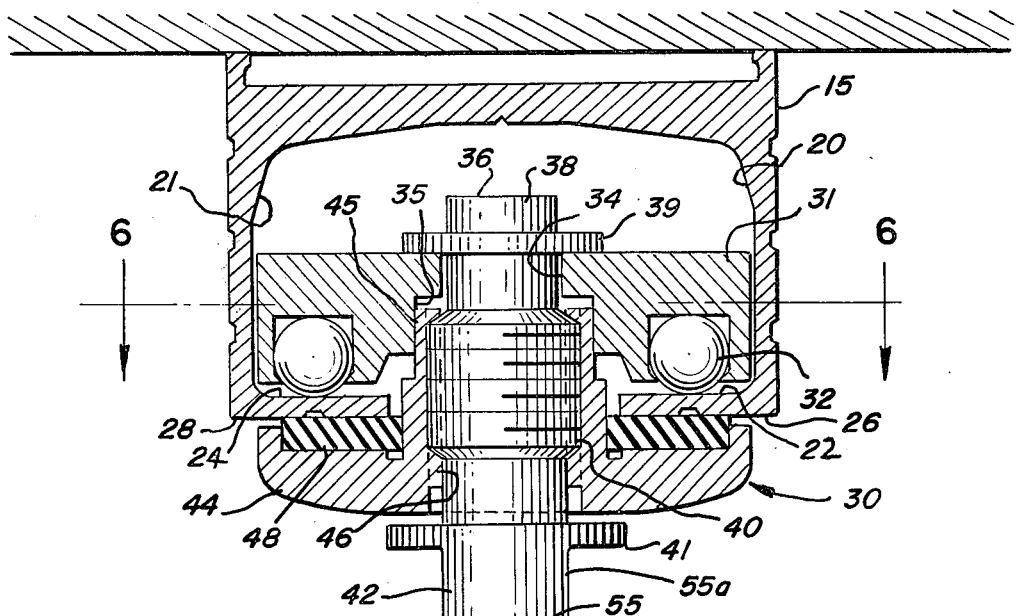
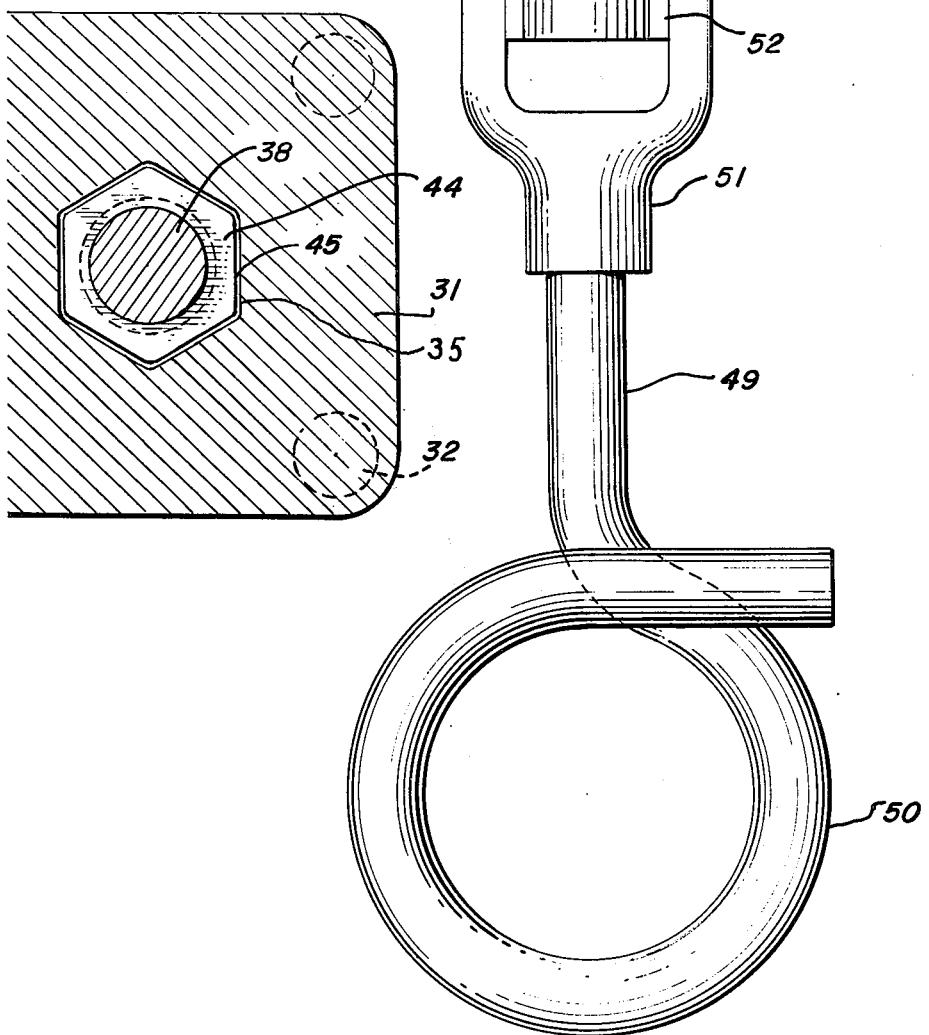
FIG. 6
FIG. 5

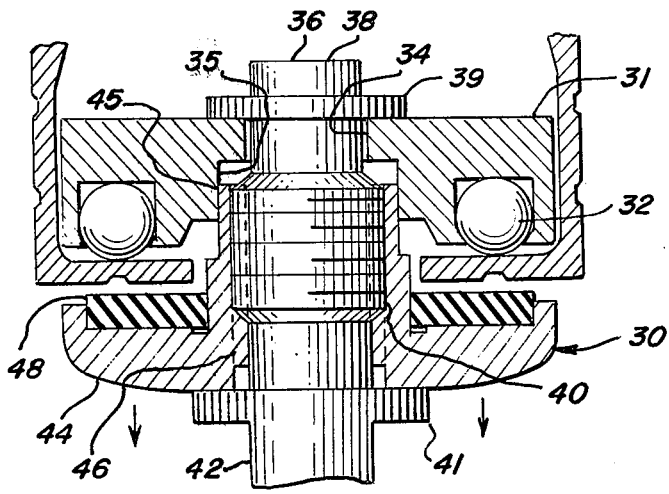
FIG. 7
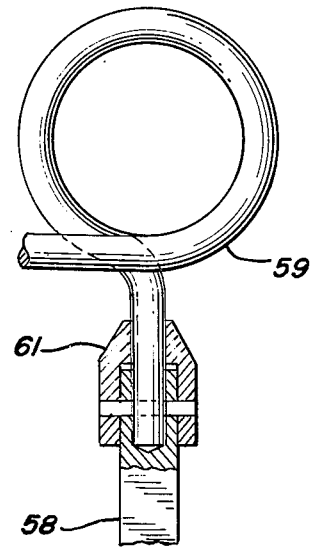
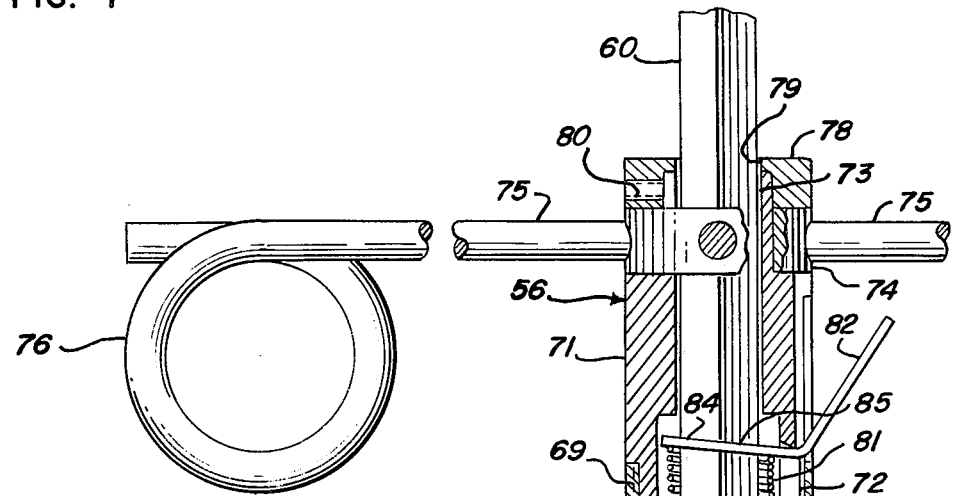
FIG. 8
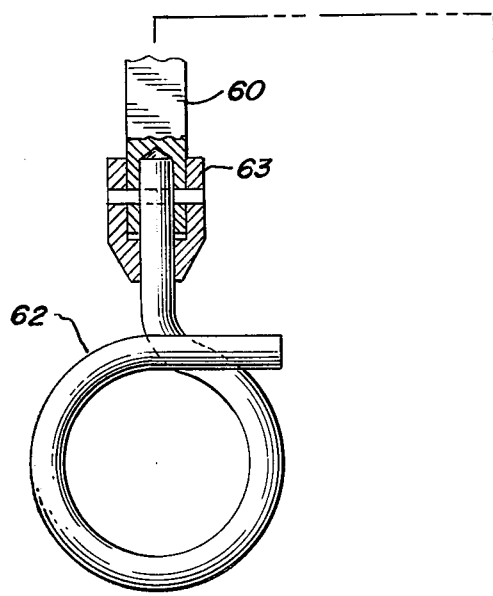
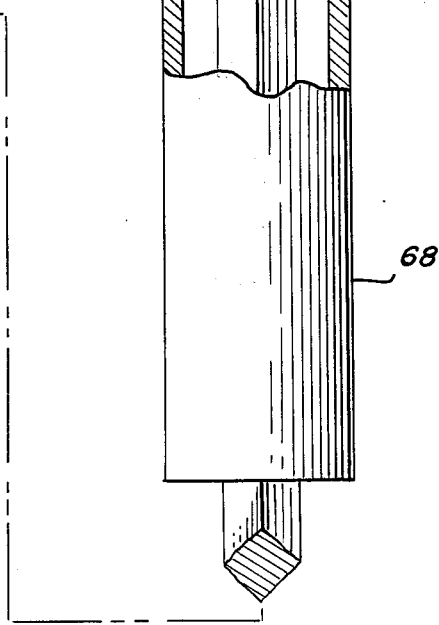

SUPPORTING APPARATUS FOR INTRAVENOUS CONTAINERS OR THE LIKE

BACKGROUND OF THE INVENTION

1. Field of the Invention

This invention pertains to apparatus for supporting containers.

2. Description of the Prior Art

Conventional apparatus for supporting containers or the like for dispensing intravenous liquids to patients frequently used in hospitals is mounted from the ceiling above the patient to maintain clear floor area and to provide a gravity feed. The apparatus includes a track for positioning the container holder and therefore the container in various parts of the room and a vertical adjustment to secure the desired container height. The vertical adjustment has posed no particular problem, but the positioning of the container holder and the maintaining of same has. Automatic locking devices actuated by placing a container of a proper weight on the apparatus and by a camming action locking an associated carriage to a track have been proposed. Generally a spring releases the locking action when the container has been removed. The automatic devices are unduly complicated; the spring must be carefully selected to be overcome by each container; and the containers cannot be moved via the apparatus until removed therefrom. Further, the tracks utilized by the carriage do not allow right angle turns by the carriage.

SUMMARY OF THE INVENTION

Applicant's apparatus has a vertical adjustment as in the prior art and is also designed to provide a locking feature that is independent of the mounting thereon of a container. Specifically, applicant has provided a track that is constructed to be mounted above the patient on the ceiling or the like. A carriage having preferably a plurality of bearing elements is included for non-rotational carriage movement along the track. Suspended for rotation from the carriage is a support member. The support member has a threaded surface which is engageable by a nut having a braking surface for engaging the track. The nut is also connected to the carriage for non-rotational motion therebetween. Also included in the apparatus is a first rod partially in the form of a hook that is connected to the support member preferably by a universal joint. A second rod for supporting a container holder is suspended from the first rod. The container holder is provided with a latch device to vertically position the holder along the second rod.

Positioning the container holder, and therefore any container mounted thereon, in relation to the track merely requires a quarter rotation of the holder. This rotation (through the aforementioned connecting elements) rotates the support member. The nut, being restrained from rotation by the carriage and the carriage by the track, rises until the braking surface contacts the track thereby locking the carriage to the track. The release of the braking surface from the track is accomplished by a counter rotation of the holder. A noteworthy feature is that by making the track restrain the carriage, which allows the nut travel, and providing mitered corners for right angle track configurations, a square carriage can be moved through the track turns preferably by the use of a universal joint. A cross over between parallel tracks is also possible. This advantage is normally not possible with the locking carriages found in the prior art.

It is, therefore, an object of this invention to provide a new and improved supporting apparatus for intravenous fluid containers or the like.

Another object of this invention is to provide a supporting apparatus having a locking feature that is operated in a conventional manner independent of the containers usable therewith.

Still another object of this invention is to provide a supporting apparatus having a locking feature that is operable with tracks having right angle configurations.

BRIEF DESCRIPTION OF THE DRAWINGS

FIG. 5 is an elevational view (partially in section) of the carriage assembly for the apparatus locked to the track;

FIG. 6 is a sectional view taken along line 6—6 of FIG. 5;

FIG. 7 is a view similar to FIG. 5 showing the carriage assembly free to move on the track; and FIG. 8 is an elevational view (partially in section) of the holder assembly for the apparatus.

DESCRIPTION OF THE PREFERRED EMBODIMENT

Figure 1:
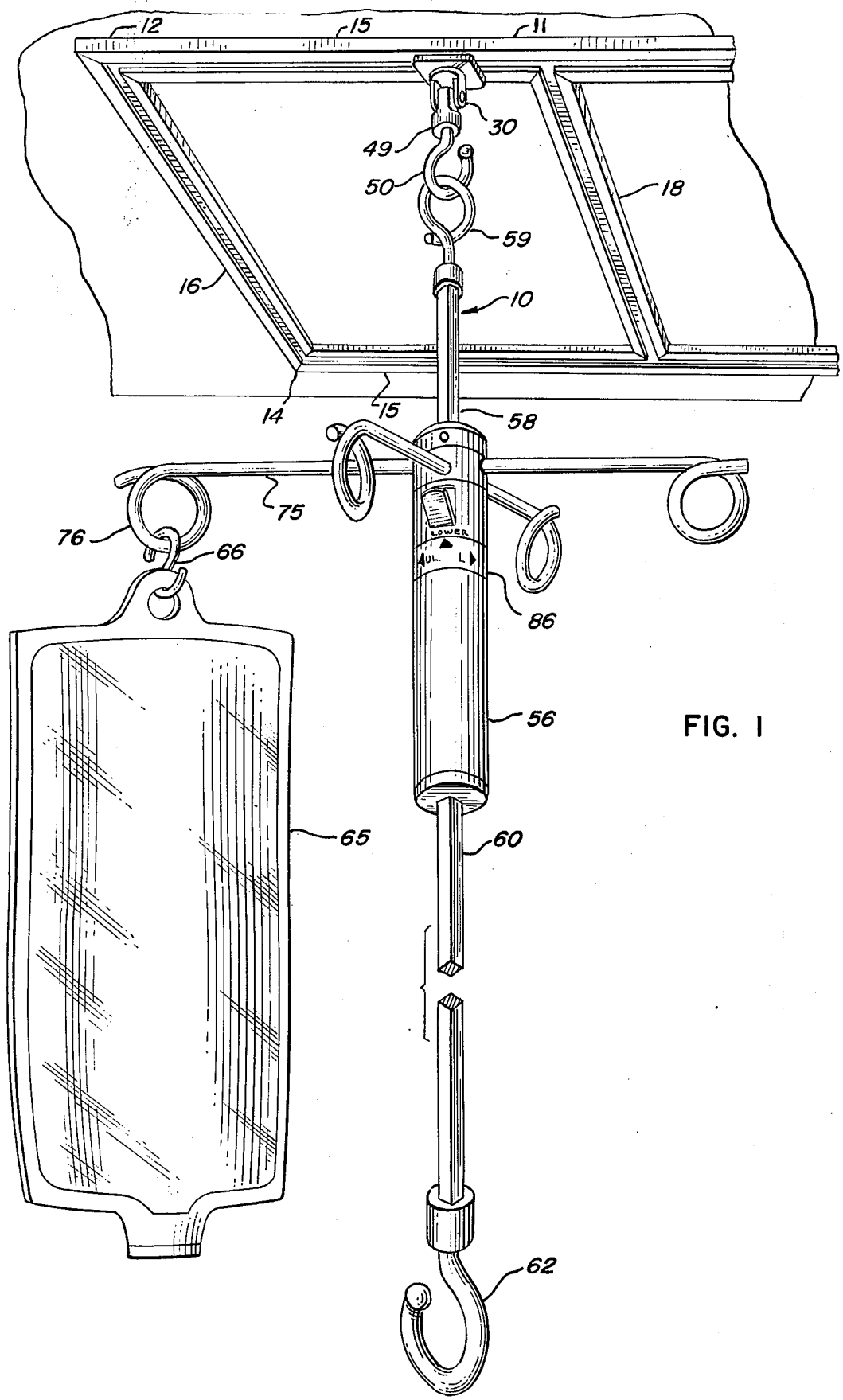
FIG. 1 is a perspective view of a supporting apparatus for containers or the like according to this invention.
Figure 2:
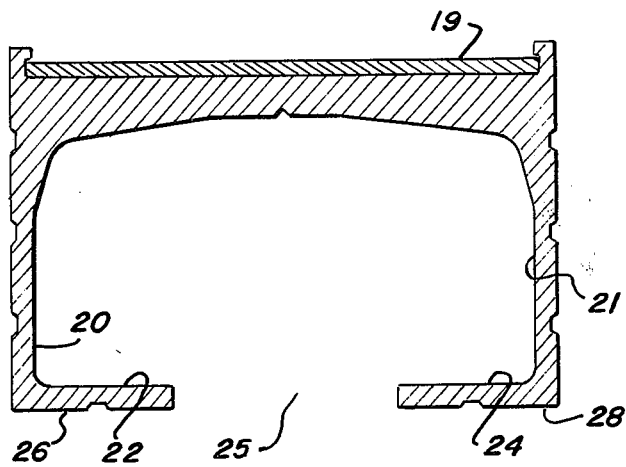
FIG. 2 is an enlarged and rotated elevational sectional view of the track for the apparatus taken along line 2—2 of FIG. 3.
Figure 3:
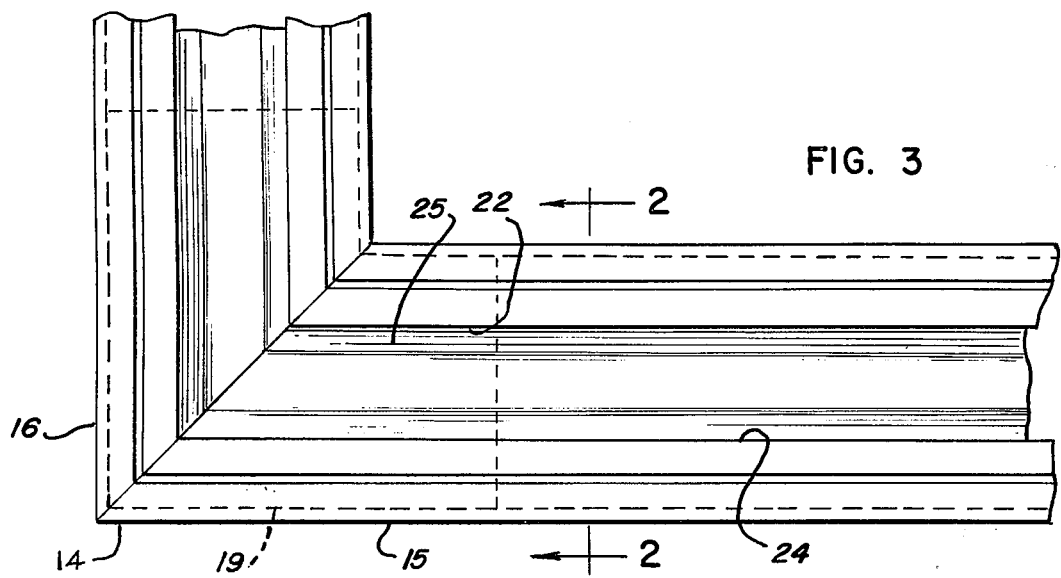
FIG. 3 is a bottom view of a corner of the track.

Referring to FIG. 1, reference numeral 10 indicates generally the supporting apparatus for intravenous containers or the like of this invention. Apparatus 10 includes track 11. Track 11, as shown, has right angle corners 12 and 14. Although the track shown can be either square or rectangular, it is obvious that straight or curved tracks could be used with the apparatus 10 of this invention. Frequently, space limitations make the use of the track shown to be most desirable. FIG. 2 discloses a sectional view of the preferred track which may be an aluminum extrusion. The track 11, as shown in FIG. 1, may be composed of track lengths 15, ends 16 and cross over sections 18. Referring to FIG. 3, corner 14 which is typical of the corners of the track 11 is produced by cutting length 15 and end 16 at a 45° angle. A suitable right angle splice plate 19 (see FIG. 3) is provided, which through appropriate fasteners, rigidly connects length 15 and end 16 together at their top surfaces. Also provided are spaced holes (not shown) through the upper track surfaces of all sections for its mounting to a room ceiling or other structure. Straight splice plates (not shown) can be used to extend the various track sections available.

As shown best in FIG. 2, all sections of track 11 are preferably of a generally C-shaped cross section. The inner portion of the C has side walls 20 and 21. The dimension between these two walls is closely held for a reason that will become evident later in this specification. Also shown in FIG. 2 are upper flange surfaces 22 and 24 with slot 25 therebetween. Surfaces 22 and 24 provide support for a later to be described carriage movable thereon. Lower flange surfaces 26 and 28 are intended to be contacted by the braking surface portion of the carriage assembly.

Referring to FIG. 3, corner 14 discloses how upper flange surfaces 22 and 24 provide a continuous path for a carriage through the right angle corner. Slot 25 also is continuous therethrough.

Figure 4:
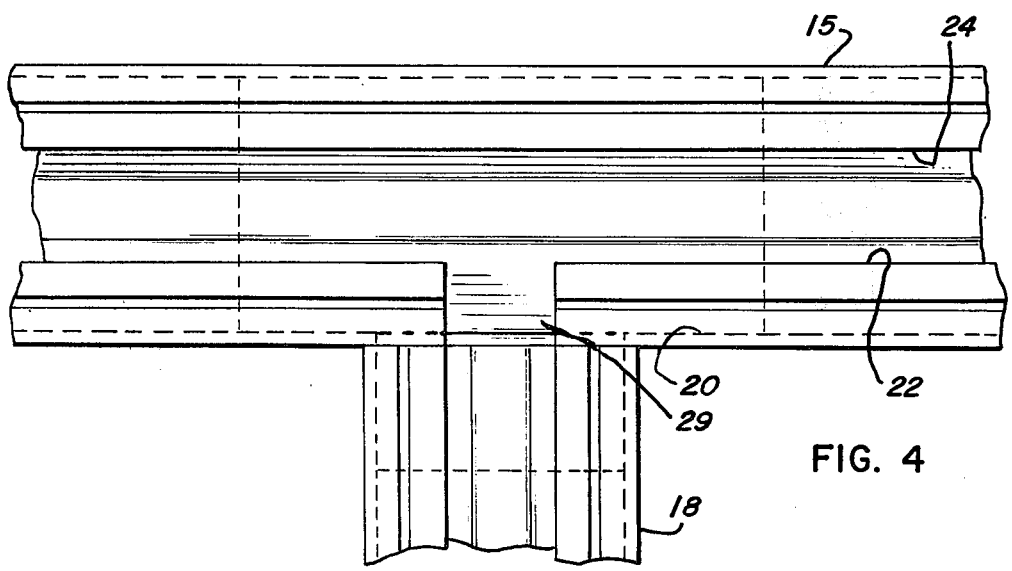
FIG. 4 is a bottom view of the junction of a track and a cross over track.

FIG. 4 discloses the junction of cross over section 18 and length 15. To provide a continuous path through the junction, passage 29 must be cut through flanged surfaces 22 and 26. Further, side wall 20 of length 15 has to be cut out to form an aperture to match the C-shaped configuration of section 18. It will be noted that passage 29 of length 15 interrupts the upper flange surfaces 22 and 26 of length 15, hence, no single continuous path through the junction into section 18 is present as in corner 14. Due to the construction of the carriage bearing elements for use therewith this does not present a problem.

Carriage assembly 30, as best shown in FIGS. 5, 6, and 7, includes carriage 31 having movable bearing elements 32 retained therein in suitable recesses. Carriage 30 has an opening 34 therethrough. Aligned with opening 34 is hex shaped receptacle 35. It will be noted that the exterior of carriage 31 has a square configuration that closely fits in the interior of C-shaped track 11. No rotation of carriage 31 in track 11 is possible. Mounted in opening 34 is a support member 36 having shaft portion 38. Retaining ring 39 fits in a suitable groove in shaft portion 38 and rotatably maintains support member 36 on carriage 31. Support member 36 has an external thread which is preferably a left hand double lead thread 40 and a shoulder 41 below the thread. A clevis 42 is also a part of support member 36. A slide nut 44 having a hex configuration 45 is adapted to fit into the hex receptacle 35 of carriage 31 to eliminate rotation therebetween. Slide nut 44 has an internal thread 46 adapted to complement thread 40 of member 36. Slide nut 44 also has a brake pad 48 which may be made of nylon fixed thereto to provide a braking surface in conjunction with lower flange surfaces 26 and 28 of track 11. Shoulder 41 provides a down stop for nut 44.

Also shown on FIG. 5 is a rod assembly 49. Rod assembly 49 has a hook end 50. Rigidly attached to rod assembly 49 at the end opposite the hook by a roll pin is rod clevis 51. Center block 52 via suitable pins 54 and pin 55 provides a universal joint 55A in conjunction with clevis 42 and rod clevis 51.

FIG. 7 shows the braking surface of 48 removed from contact with the lower flange surfaces of track 11.

Holder assembly 56 shown in FIG. 1 and also FIG. 8 is combined with support rod assembly 58. Support rod assembly 58 has an upper hook end 59 that is adapted to be mounted on hook 50 of rod assembly 49. Hook end 59 is attached to square support rod 60 by a collar 61 and a roll pin to form an integral unit. Lower hook end 62 is similarly attached to rod 60 by collar 63 and a roll pin. End 62 can be used to support a container as other support rods later to be described.

Mounted on rod 60 is holder assembly 56 as is best shown in FIG. 8. Holder assembly 56 provides support for an intravenous container 65 or the like supported by a bail 66 (see FIG. 1) besides including a vertical adjustment in regard to rod 60. Holder assembly 56 includes handle bottom 68 having an opening for the rod 60 therethrough and an upper interval thread 69. Located below thread 69 is washer 70. Handle top 71 having external thread 72 is threaded along with the use Loctite or similar material to handle bottom 68. Handle top 71 has extended neck 73 on which is mounted for free rotation hanger rod bearing 74. Bearing 74 has openings for four rods 75 which are rigidly fixed thereto by roll pins (not shown). Each rod terminates in a hook end 76 from which may be hung a bail 66 for a container 65. Maintaining rod bearing 74 on neck 73 is top cap 78. Cap 78 has a square hole 79 adapted to complement square rod 60. Cap 78 is held rigid with handle top 71 by setscrew 80. Because of the construction of cap 78, rotation of handle bottom 68 and handle top 71 threaded thereto causes rotation of rod 60. As mentioned previously hanger rod bearing 74 and its rods 75 are unaffected by rotation of handle top 71.

As shown best in FIG. 8 a vertical adjustment is included in holder assembly 56. The adjustment feature includes spring 81 extending between washer 70 and locking lever 82. Lever 82 has a right angle configuration with a square hole 84 in one leg 85. Leg 85 extends into the interior of handle top 71 through a suitable opening. In the locking position, spring 81 maintains leg 85 against the opening in wall of 71 and forces the other end of the leg upward to wedge against square rod 60. Holder assembly 56 is thus locked in position at a desired elevation on rod 60. To raise holder assembly 56, lever 82 need not be moved, as physically moving the holder assembly tends to straighten leg 85 thereby relieving the wedging action of the locking lever 82 to free same. To lower the holder assembly, requires the depressing of lever 82 where same extends away from holder assembly 56 in the locked position. Depressing lever 82 rotates leg 85 downward thereby relieving the wedging action. It is to be noted that holder assembly 56 is held during the process, thus the holder assembly cannot fall freely. A suitable decal 86 (FIG. 1) provides instructions for the vertical positioning of holder assembly 56 and also the locking of the holder assembly in regard to track 11.

In operation, the carriage assembly 30 including the rod assembly 49 is placed in an open end of track 11 after same has been assembled on a ceiling for example. If an open track is to be utilized, suitable stops (not shown) with flexible bumpers can be installed. If not, preferably an end 16 of track 11 must be installed after the carriage assembly to close track 11. With the carriage assembly 30 as shown in FIG. 1 and FIG. 7, the carriage is free to move along track 11. The holder assembly 56 including support rod assembly 58 is then mounted on the hook 50 of rod assembly 49. A container 65 via a bail can be hung at this point on a rod 75 at hook 76 mounted on rod bearing 74. With the carriage assembly free to move, the operator by grasping the holder assembly 56 can, by means of the universal joint 55a, work the carriage along the length 15 of track 11 and through the square corner 12 to the end 16 and back to the opposing length 15. If a cross over 18 is provided, the carriage can also be moved thereover from a length 15. Of course, curved portions of the track can be combined with the track shown. When the desired holder assembly and therefore container position is achieved, the operator by a quarter rotation to the right as noted on the decal 86 of the holder assembly 56 locks the carriage assembly 30 to track 11. This is because rotating the holder assembly 56, in turn, rotates the rod assembly 58, the rod assembly 49 and through the universal joint 55a support member 36. Member 36 cannot advance and nut 44 cannot rotate since restrained by the mating hex receptacle 35 of the carriage 31 which in turn cannot rotate in track 11, hence nut 44 rises and presses brake pad 48 against lower flange surfaces 26 and 28 of track 11. Holder assembly 56 and carriage assembly 31 are thus locked in position on track 11. A contrary quarter rotation of holder assembly 56 will free carriage assembly 30 from track 11.

The vertical positioning of the holder can be achieved by the procedure previously detailed.

By providing the restraints shown in the preferred embodiment for the rotation of nut via the carriage and the carriage by the track, applicant has provided a locking feature in regard to the carriage and track with a carriage that is adapted to be moved through square corners.

From the foregoing, it should be apparent that applicant has provided an apparatus that will operate in a straight forward manner with minimum distraction to personnel over a varied track configuration to secure almost any conceivable positioning capability.

I claim:
1. A supporting apparatus for containers comprising:
   a. a track adapted to be fastened to a ceiling, said track having a generally C-shaped cross section, said track having mitered joints to provide right angle turns;
   b. a square carriage mounted for non-rotational movement in said track;
   c. a support member having a shaft extending into said track through the opening in the C-shaped cross section, said shaft rotatably mounting said member on said carriage below said track, said shaft having an external thread;
   d. a nut having a braking surface, said nut engaging said thread, said nut being connected to said carriage for non-rotational motion therebetween;
   e. a first rod movably connected to said support member by a universal joint;
   f. a second rod releasably connected to said first rod; and
   g. a container holder having at least one container support mounted thereon, said holder being connected to said second rod for rotation therewith, said holder upon rotation also rotating said first and second rods and said support member to raise said nut to move said braking surface against said track to lock said carriage to said track, and opposite rotation lowering said braking surface from said track and allowing movement of said holder and square carriage via said universal joint through the right angle turns in said track.

2. The apparatus of claim 1 in which said thread and said nut are left hand whereby rotating said holder clockwise raises said braking surface to contact said track and rotating said holder counterclockwise lowers said braking surface from said track and in which said support member has a shoulder to act as a stop when said braking surface is lowered.

3. The apparatus of claim 2 further comprising means for releasably connecting said holder to said second rod for upward or downward positioning thereon.

4. The apparatus of claim 3 in which said container support is rotatably mounted on said holder and in which said nut braking surface is made of nylon.

5. The apparatus of claim 4 in which said track further comprises cross over tracks connected between parallel tracks at right angles thereto and in which each of said parallel tracks has an aperture through a side matching the C-shaped cross section of the adjacent cross-over track and also a passage in the lower flange of the C section also adjacent the cross over track for the movement therethrough of the carriage and the support member.

* * * * *